United States Patent
Lennon et al.

(10) Patent No.: US 9,891,219 B2
(45) Date of Patent: Feb. 13, 2018

(54) METHODS FOR TREATING NEUROMYELITIS OPTICA (NMO) BY ADMINISTRATION OF ECULIZUMAB TO AN INDIVIDUAL THAT IS AQUAPORIN-4 (AQP4)-IGG AUTOANTIBODY POSITIVE

(75) Inventors: Vanda A. Lennon, Rochester, MN (US); Shannon Hinson, Rochester, MN (US); Sean J. Pittock, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 465 days.

(21) Appl. No.: 12/573,942

(22) Filed: Oct. 6, 2009

(65) Prior Publication Data

US 2010/0092478 A1 Apr. 15, 2010

Related U.S. Application Data

(60) Provisional application No. 61/104,621, filed on Oct. 10, 2008.

(51) Int. Cl.
| | |
|---|---|
| *G01N 33/53* | (2006.01) |
| *A61K 39/00* | (2006.01) |
| *A61K 49/00* | (2006.01) |
| *A61K 38/00* | (2006.01) |
| *G01N 33/564* | (2006.01) |
| *A61K 31/439* | (2006.01) |
| *A61K 39/395* | (2006.01) |
| *A61K 45/06* | (2006.01) |

(52) U.S. Cl.
CPC ......... *G01N 33/564* (2013.01); *A61K 31/439* (2013.01); *A61K 39/395* (2013.01); *A61K 45/06* (2013.01); *G01N 2333/705* (2013.01); *G01N 2800/285* (2013.01); *G01N 2800/52* (2013.01)

(58) Field of Classification Search
CPC ............ A61K 2300/00; A61K 39/0008; A61K 2039/505; A61K 47/48384; A61K 47/48561; A61K 39/395; A61K 47/48715; A61K 47/48376; A61K 49/0058; C07K 16/18; C07K 2317/24; C07K 2317/76; C07K 2317/56; C07K 16/00; C07K 2317/565; C07K 2317/622; C07K 2317/734; C07K 14/472; C07K 16/468; C07K 2317/55; C07K 2317/64; C07K 2318/10; C07K 14/4713; C07K 2317/54; G01N 2333/4716; G01N 2800/28; G01N 33/6854

See application file for complete search history.

(56) References Cited

U.S. PATENT DOCUMENTS

| | | | | |
|---|---|---|---|---|
| 5,506,247 A | * | 4/1996 | Sindelar | C07D 307/94 514/374 |
| 6,572,867 B1 | * | 6/2003 | Schwarz | A61K 39/001 424/184.1 |
| 7,101,679 B2 | * | 9/2006 | Lennon et al. | 435/7.21 |
| 7,592,326 B2 | * | 9/2009 | Karaolis | 514/47 |
| 7,601,335 B2 | * | 10/2009 | McCutcheon et al. | 424/9.2 |
| 7,659,312 B2 | * | 2/2010 | Nakada et al. | 514/601 |
| 2003/0208058 A1 | | 11/2003 | Fiscella et al. | |
| 2004/0102525 A1 | * | 5/2004 | Kozachuk | 514/662 |
| 2005/0226870 A1 | * | 10/2005 | Wang | C07K 16/18 424/143.1 |
| 2006/0258721 A1 | * | 11/2006 | Maddaford et al. | 514/365 |
| 2006/0263349 A1 | * | 11/2006 | McCutcheon et al. | 424/131.1 |
| 2007/0178068 A1 | * | 8/2007 | Reich | C12N 15/113 424/93.2 |
| 2007/0197511 A1 | * | 8/2007 | Brimble et al. | 514/224.2 |
| 2009/0104189 A1 | | 4/2009 | Yu et al. | |
| 2009/0269356 A1 | | 10/2009 | Epstein et al. | |
| 2009/0324585 A1 | * | 12/2009 | Robinson | A01K 67/0278 514/1.1 |
| 2010/0021416 A1 | * | 1/2010 | Lichter | A61K 9/0046 424/78.17 |
| 2014/0030262 A1 | | 1/2014 | Lennon et al. | |
| 2015/0104813 A1 | | 4/2015 | Lennon | |

OTHER PUBLICATIONS

Roemer et al. Brain, 2007; 130:1194-1205.*
Jacob et al. J. Neuroimmunol. 2007; 126-138.*
Abbott et al., "Astrocyte-endothelial interactions at the blood-brain barrier," *Nat Rev Neurosci.*, 2006, 7:41-53.
Amiry-Moghaddamand and Ottersen, "The molecular basis of water transport in the brain," *Nat Rev Neurosci.*, 2003, 4:991-1001.
Bell et al., "A comparison of serologic reactivity among SLE patients with or without anti-Ro (SS-A) antibodies," *J Rheumatol.*, 1984, 11(3):315-317.
Bhat et al., "Axon-glia interations and the domain organization of myelinated axons requires neurexin IV/Caspr/Paranodin," *Neuron*, 2001, 30:369-383.
Cree et al., "An open label study of the effects of nituximab in neuromyelitis optica," *Neurology*, 2005, 64(7):1270-1272.
de Petris and Raff, "Normal distribution, patching and capping of lymphocyte surface immunoglobulin studied by electron microscopy," *Nature New Biology*, 1973, 241(113):257-259.
Debus et al., "Monoclonal antibodies specific for glial fibrillary acidic (GFA) protein and for each of the neurofilament triplet polypeptides," *Differentiation*, 1983, 25:193-203.
Farkas et al., "CD59 blocks not only the insertion of C9 into MAC but inhibits ion channel formation by homologous C5b-8 as well as C5b-9," *J Physiol*, 2002, 539:537-545.
Garlin et al., "Pharmacology of Sodium-Dependent High-Affinity 1-[3H]Glutamate Transport in Glial Cultures," *J. Neurochem.*, 1995, 64:2572-2580.

(Continued)

*Primary Examiner* — Chang-Yu Wang
(74) *Attorney, Agent, or Firm* — Fish & Richardson P.C.

(57) ABSTRACT

The invention provides prognostic methods for evaluating the severity of NMO and NMO-associated diseases as well as methods of treating NMO and NMO-associated diseases.

6 Claims, 4 Drawing Sheets

(56) References Cited

OTHER PUBLICATIONS

Hinson et al., "Pathogenic potential of IgG binding to water channel extracellular domain in neuromyelitis optica," *Neurology*, 2007, 69:2221-2231.
Jarius et al., "NMO-IgG in the diagnosis of neuromyelitis optica," *Neurology*, 2007, 68:1076-1077.
Jensen and Braeuner-Osborne, "Pharmacological characterization of human excitatory amino acid transporters EAAT1, EAAT2 and EAAR3 in a fluorescence-based membrane potential assay," *Biochem. Pharmacol.*, 2004, 67:2115-2127.
Kasibhatla et al., "Propidium Iodide (PI) Uptake Assay to Detect Apoptosis," *Cold Spring Harb Protoc*; 2006, 2 pages.
Keegan et al., "Plasma exchange for severe attacks of CNS demyelination: predictors of response," *Neurology*, 2002, 58:143-146.
Landis and Reese, "Arrays of particles in freeze-fractured astrocytic membranes," *J Cell Biol.*, 1974, 60:316-320.
Lennon et al., "A serum autoantibody marker of neuromyelitis optica: distinction from multiple sclerosis," *Lancet*, 2004, 364:2106-2112.
Lennon et al., "IgG marker of optic-spinal multiple sclerosis binds to the aquaporin-4 water channel," *J Exp Med.*, 2005, 202(4):473-477.
Lennon et al., "Membrane array of acetylcholine receptors determines complement-dependent mononuclear phagocytosis in experimental myasthenia gravis," *Fed Proc.*, 1984, 43:1764.
Lin et al., "Modulation of the neuronal glutamate transporter EAAC1 by the interacting protein GTRAP-3-18," *Nature*, 2001, 410:84-88.
Louis et al., "CG-4, a new bipotential glial cell line from rat brain, is capable of differentiating in vitro into either mature oligodendrocytes or type-2 astrocytes," *J. Neurosci. Res.*, 1992, 31:193-204.
Lucchinetti et al. "A role for humoral mechanisms in the pathogenesis of Devie's neuromyelitis optica," *Brain*, 2002, 125:1450-1461.
McDonald et al., "Oligodendrocytes from forebrain are highly vulnerable to AMPA/kainate receptor-mediated excitotoxicity," *Nat Med.*, 1998, 4(3):291-297.
McKeon, "CNS aquaporin-4 autoimmunity in children," *Neurology*, 2008, 71:93-100.
Meri et al. "Human protectin (CD59), an 18,000-20,000 MW complement lysis restricting factor, inhibits C5b-8 catalysed insertion of C9 into lipid bilayers." *Immunology*, 1990, 71:1-9.
Misu et al., "Loss of aquaporin-4 in active perivascular lesions in neuromyelitis optica: A case report," *Tohoku J Exp Med.*, 2006, 209:269-275.
Morgan and Gasque, "Expression of complement in the brain: role in health and disease," *Immunol Today*, 1996, 17(10):461-466.
Pitt et al., "Glutamate excitotoxicity in a model of multiple sclerosis," *Nat Med*., 2000, 6(1):67-70.
Pittock et al., "Brain abnormalities in neuromyelitis optica," *Arch Neurol.*, 2006, 63: 390-396.
Pittock et al., "Neuromyelitis optica and non-organ-specific autoimmunity," *Arch Neurol.*, 2008, 65(1):78-83.
Pittock et al., "Neuromyelitis optica brain lesions localized at sites of high aquaporin 4 expression," *Arch Neurol.*, 2006, 63:964-968.
Raff et al., "A glial progenitor cell that develops in vitro into an astrocyte or an oligodendrocyte depending on culture medium," *Nature*, 1983, 303:390-396.
Rasband et al., "Dependence of nodal sodium channel clustering on paranodal axoglial contact in the developing CNS," *J Neurosci.*, 1999, 19(17):7516-7528.
Rash et al., "Freeze-fracture and immunogold analysis of aquaporin-4 (AQP4) square arrays, with models of AQP4 lattice assembly," *Neuroscience*, 2004, 129(4):915-934.
Roemer et al., "Pattern-specific loss of aquaporin 4 immunoreactivity distinguishes neuromyelitis optica from multiple sclerosis," *Brain*, 2007, 130:1194-1205.
Salter and Fern, "NMDA receptors are expressed in developing oligodendrocyte processes and mediate injury," *Nature*, 2005, 438:1167-1171.
Smith et al., "Autoimmune encephalomyelitis ameliorated by AMPA antagonists," *Nat Med.*, 2000, 61:62-66.
Takahashi et al., "Establishment of a new sensitive assay for anti-human aquaporin-4 antibody in neuromyelitis optica," *Tohoku J Exp Med.*, 2006, 210:307-313.
Walport, "Complement: First of Two Parts," *N Engl J Med.*, 2001, 344(14):1058-1066.
Wingerchuck et al., "Revised diagnostic criteria for neuromyelitis optica," *Neurology*, 2006, 66:1485-1489.
Wingerchuck et al., "The spectrum of neuromyelitis optica," *Lancet Neurol.*, 2007, 6:805-815.
Wingerchuk et al., "The clinical course of neuromyelitis optica (Devie' syndrome)," *Neurology*, 1999, 53:1107-1114.
Zeng et al., "Aquaporin-4 deficiency down regulates glutamate uptake and GLT-1 expression in astrocytes," *Mol Cell Neurosci*, 2007, 34:34-39.
Zuliani et al., "NMO-IgG antibodies in neuromyelitis optica: a report of 2 cases," *Neurologia*, 2006, 21:314-317.
Pittock et al., "Eculizumab in AQP4-IgG-positive relapsing neuromyelitis optica spectrum disorders: an open-lael pilot study," *Lancet Neurol.*, 12(6):554-562, Epub Apr. 26, 2013.
Roemer et al., "Pattern-specific loss of aquaporin-4 immunoreactivity distinguishes neuromyelitis optica from multiple sclerosis," Brain., 130(Pt 5):1194-1205. Epub Feb. 4, 2007.
Wingerchuk et al., "The spectrum of neuromyelitis optica," Lancet Neurol., 6(9):805-815, Sep. 2007.
Burgess et al., "Possible dissociation of the heparin-binding and mitogenic activities of heparin-binding (acidic fibroblast) growth factor-1 from its receptor-binding activities by site-directed mutagenesis of a single lysine residue," *J Cell Biol.*, 111(5 Pt 1):2129-2138, Nov. 1990.
Kim et al., "Clinical efficacy of plasmapheresis in patients with neuromyelitis optica spectrum disorder and effects on circulating anti-aquaporin-4 antibody levels," J Clin Neurol., 9(1):36-42, Epub Jan. 3, 2013.
Kim et al., "Utility of aquaporin-4 antibody assay in patients with neuromyelitis optica spectrum disorders," *Multiple Sclerosis Journal*, DOI: 10.1177/1352458512472748, Jan. 17, 2013, 8 pages.
Pawson et al., "Assembly of cell regulatory systems through protein interaction domains," *Science*, 300(5618):445-452, Apr. 18, 2003.

* cited by examiner

METHODS FOR TREATING NEUROMYELITIS OPTICA (NMO) BY ADMINISTRATION OF ECULIZUMAB TO AN INDIVIDUAL THAT IS AQUAPORIN-4 (AQP4)-IGG AUTOANTIBODY POSITIVE

CROSS REFERENCE TO RELATED APPLICATIONS

This application claims priority under 35 U.S.C. § 119(e) of U.S. Application No. 61/104,621, filed Oct. 10, 2008.

FEDERALLY SPONSORED RESEARCH OR DEVELOPMENT

This invention was made with government support under Grant No. NS049577 awarded by National Institutes of Health. The government has certain rights in the invention.

TECHNICAL FIELD

This disclosure generally relates to autoimmune diseases.

BACKGROUND

Neuromyelitis optica (NMO) is currently the best defined acquired inflammatory demyelinating disorder of the central nervous system (CNS). NMO attacks optic nerves and spinal cord selectively and repeatedly. Clinical, histopathological and immunobiological observations support a pathogenic role for an IgG autoantibody specific for the astrocytic water channel aquaporin-4 (AQP4), and the severity of acute NMO is ameliorated by antibody-depleting therapies.

In contrast to most inflammatory CNS demyelinating disorders, tissue destruction in NMO is profound. In addition to white matter lesions, NMO characteristically exhibits central necrosis of spinal cord gray matter. Histopathological CNS lesions lack AQP4 and show deposition of IgM and IgG and products of complement activation in a vasculocentric pattern that coincides with the normal distribution of AQP4.

Until recently, NMO was considered a rare and severe variant of multiple sclerosis (MS). However, the advent of serological testing for AQP4-IgG has revealed that NMO and its inaugural forms are more common than previously recognized. They tend to be misdiagnosed as MS, which lacks a specific biomarker.

SUMMARY

This disclosure provides prognostic methods for evaluating the severity of NMO and NMO-associated diseases as well as methods of treating NMO and NMO-associated diseases.

In one aspect, methods of providing a prognosis for an individual that has NMO or a NMO-associated disease are provided. Such methods typically include providing a biological sample from the individual; and determining, in vitro, whether or not the biological sample reduces cell surface expression of EAAT2 or reduces uptake of extracellular glutamate compared to a biological sample from an individual that does not have NMO or a NMO-associated disease. Typically, a reduction in cell surface expression of EAAT2 or a reduction in uptake of extracellular glutamate correlates with a prognosis of the individual.

In another aspect, methods of providing a prognosis for an individual that has NMO or a NMO-associated disease are provided. Such methods generally include providing a biological sample from the individual; contacting the biological sample with primary astrocytes, a differentiated astrocyte-type cell, or a non-astrocytic cell expressing a gene encoding aquaporin-4 or a functional fragment thereof; and determining, in vitro, whether or not the biological sample reduces cell surface expression of EAAT2 or reduces uptake of extracellular glutamate compared to a biological sample from an individual that does not have NMO or a NMO-associated disease. Generally, a reduction in cell surface expression of EAAT2 or a reduction in uptake of extracellular glutamate correlates with a prognosis of the individual.

Representative biological samples include serum, plasma, cerebrospinal fluid (CSF), and immunoglobulins.

In still another aspect, methods of providing a prognosis for an individual that has NMO or a NMO-associated disease are provided. Such methods typically include providing a biological sample from the individual; contacting the biological sample with cells or tissues in the presence of aquaporin-4 polypeptides or functional fragments thereof; and determining whether or not complement is activated in the cells. Generally, an activation of complement correlates with a prognosis of the individual. In one embodiment, the aquaporin-4 polypeptides or functional fragments thereof are expressed by the cells.

In one aspect, methods of treating an individual that has NMO are provided. Such methods can include administering a glutamate receptor antagonist to the individual. Representative glutamate receptor antagonists include 1-amino-3,5-dimethyl-adamantane, 1-aminoadamantane, (+)-3-methoxy-17-methyl-(9α,13α,14α)-morphinan, 17-methyl-9a,13a,14a-morphinan-3-ol, 2-(2-chlorophenyl)-2-methylamino-cyclohexan-1-one, 1-(1-phenylcyclohexyl)piperidine, (±)cis-2-[(dimethylamino)methyl]-1-(3-methoxyphenyl)cyclohexanol hydrochloride, and 6-(Dimethylamino)-4,4-diphenylheptan-3-one. Such methods can further include administering a compound to the individual that inhibits complement.

In still another aspect, methods of treating an individual that has NMO are provided. Such methods typically include administering a compound to the individual that inhibits complement. Representative compounds that inhibit complement include Compstatin, APT070(MICROCEPT), soluble complement receptor 1 (sCR1), anti-C5 antibody, eculizumab (SOLARIS®), and substituted dihydrobenzofurans, spirobenzofuran-2(3H)-cycloalkanes, and their open chain intermediates. Such methods can further include administering a glutamate receptor antagonist to the individual.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 2 are graphs that demonstrate that, in primary astrocytes, NMO-IgG impaired glutamate uptake or complement activation. (A) Quantitation of membrane permeability after exposure to control or NMO serum. Increase in permeability to propidium iodide (PI)>2 fold by NMO serum required active complement (ΔC'=inactivated complement). (B) Uptake of L-[$^3$H]glutamate (±Na+-containing buffer) without human serum (open box) or in control (shaded box) or NMO serum (hatched box). Excess unlabeled glutamate (dark box) prevented L-[$^3$H]glutamate uptake. NMO serum reduced L-[$^3$H]glutamate uptake by 50%. Experiment (B) was performed twice. All others were performed at least 3 times.

DETAILED DESCRIPTION

NMO-IgG is a clinically validated serum biomarker that distinguishes relapsing CNS inflammatory demyelinating disorders related to neuromyelitis optica (NMO) from multiple sclerosis (MS). This autoantibody targets astrocytic aquaporin-4 (AQP4) water channels. Characteristic CNS lesions exhibit selective depletion of AQP4, with and without associated myelin loss, focal vasculocentric deposits of IgG, IgM and complement, prominent edema and inflammation.

A marked reduction of the astrocytic Na+-dependent excitatory amino acid transporter, EAAT2 (a homolog of rodent GLT-1 (Zeng et al., 2007, *Mol. Cell. Neurosci.*, 34:34-9) in AQP4-deficient regions of NMO patient spinal cord lesions is described. Thus, binding of NMO-IgG to astrocytic AQP4 appears to initiate several potentially neuropathogenic mechanisms: complement activation and AQP4 and EAAT2 down-regulation. Since EAAT2 accounts for >90% of glutamate uptake in the CNS, is critical for clearing glutamate from excitatory synapses and is expressed selectively in astrocytes, altered expression of EAAT2 can impair glutamate homeostasis, resulting in over-stimulation of glutamate receptors in neurons and oligodendrocytes. This disruption in glutamate homeostasis may contribute indirectly to the pathobiology of NMO or NMO-associated diseases. See, for example, Hinson et al. 2007, *Neurology*, 69:2221-31.

NMO and NMO-associated diseases encompass a number of neurological disorders related to AQP4 autoimmunity. For example, NMO diseases are represented by a spectrum of adult or pediatric inflammatory CNS demyelinating disorders related to AQP4 autoimmunity involving longitudinally extensive transverse myelitis, optic neuritis (e.g., relapsing optic neuritis) or brainstem encephalitis. Representative NMO-associated diseases include connective tissue disorders related to AQP4 autoimmunity (e.g., Lupus or Sjogrens syndrome) and cancers related to AQP4 autoimmunity (e.g., breast).

Prognostics

The relationship described herein between aquaporin-4 and EAAT2 and the associated loss of EAAT2 in NMO or NMO-associated diseases can be used in the prognosis of an individual. For example, the amount of reduction in cell surface expression of EAAT2 or the amount of reduction in the uptake of extracellular glutamate can be correlated with the severity of the NMO or NMO-associated disease or the accompanying symptoms.

Well known in vitro bioassays can be used to evaluate whether or not a reduction in cell surface expression of EAAT2 or uptake of extracellular glutamate is observed. For example, a biological sample from an individual can be contacted with primary astrocytes, differentiated astrocyte-type cells, or non-astrocytic cells expressing a gene encoding aquaporin-4 or a functional fragment thereof, and either or both cell surface expression of EAAT2 or the uptake of extracellular glutamate by the cells can be evaluated. Cell surface expression can be evaluated using well known immunoassays such as innumohistochemistry or Western blot (*Immunoassay*, 1996, Diamandis & Christopoulos, Eds., Academic Press), and glutamate uptake by a cell can be evaluated, for example, using methods such as those described by Lin et al., 2001, *Nature*, 410:84-8.

A reduction in the cell surface expression of EAAT2 or a reduction in the uptake of extracellular glutamate (compared to the cell surface expression of EAAT2 or the glutamate uptake that occurs in the presence of a biological sample from an individual that does not have NMO or a NMO-associated disease) can be used prognostically. Typically, the amount of reduction in either or both the cell surface expression of EAAT2 and the uptake of extracellular glutamate is directly related to the severity of the NMO or NMO-associated disease that the individual will experience.

In addition, the involvement of complement activation in NMO and NMO-associated diseases can be used in the prognosis of an individual suffering from NMO or a NMO-associated disease. For example, the extent or degree that complement is activated in the presence of serum (or components therein) from an individual from an individual that has NMO or a NMO-associated disease (compared to the extent or degree that complement is activated in the presence of serum (or components therein) from an individual that does not suffer from NMO or a NMO-associated disease) can be correlated with the severity of disease.

Methods for evaluating whether or not complement is activated in the presence of a biological sample from an individual are known in the art. Such methods include, without limitation, exposing the biological sample to cells or tissues in the presence of aquaporin-4 polypeptides (or functional fragments thereof), and determining whether or not complement is activated in the cells. For example, activation of complement by cells can be determined by evaluating cells for propidium iodide uptake (Kasibhatla et al., 2006, *Cold Spring Harb. Protoc.*; doi: 10.1101/pdb.prot4495) or using immunoassays (e.g., immunohistochemistry) to detect the deposition or accumulation of one or more components of complement (e.g., C9neo assembly or C5 deposition).

Any number of biological samples can be used in the methods described herein. For example, a biological sample can include, without limitation, serum, plasma, and cerebrospinal fluid (CSF). In addition, a biological sample can include immunoglobulins (e.g., engineered immunoglobulins or immunoglobulins that are secreted by cultured B lymphocytes or plasma cells). Alternatively, under autopsy conditions, biological samples can include tissue biopsies such as from spinal cord and brain.

It would be understood by those of skill in the art that, under conditions described herein in which aquaporin-4 polypeptides or functional fragments are required, such polypeptides or fragments can be naturally present in the cells (e.g., endogenously expressed or native), or cells can be genetically engineered to express aquaporin-4 polypeptides or functional fragments thereof. In addition, aquaporin-4 polypeptides or functional fragments thereof (e.g., purified aquaporin-4 or functional fragments thereof) can be added exogenously to the cells, to the biological sample, or to a combination of the two.

Thereapeutics

The relationship described herein between EAAT2 and/or complement activation with NMO-IgG provides a number of novel therapies for treating NMO or NMO-associated diseases. For example, in some instances, an individual can be administered an effective amount of an antagonist of glutamate receptors can be administered to an individual. In some instances, the antagonists are specific for glutamate receptors, and in other instances, the antagonists are specific for glutamate receptors on neurons, oligodendrocytes and astrocytes. An effective amount of an antagonist of glutamate receptors is an amount that reduces or eliminates the neurological effects caused by the accumulation of extracellular glutamate.

Antagonists or glutamate receptors, also referred to as glutamate receptor blockers, include, without limitation, 1-amino-3,5-dimethyl-adamantane (MEMANTINE®), 1-aminoadamantane (AMANTADINE®), (+)-3-methoxy-17-methyl-(9α,13α,14α)-morphinan (DEXTROMETHORPHAN®), 17-methyl-9a,13a,14a-morphinan-3-ol (DEXTRORPHAN®), 2-(2-chlorophenyl)-2-methylaminocyclohexan-1-one(KETAMINE®), 1-(1-phenylcyclohexyl) piperidine (PHENCYCLIDINE®), (±)cis-2-[(dimethylamino)methyl]-1-(3-methoxyphenyl) cyclohexanol hydrochloride (TRAMADOL®), and 6-(Dimethylamino)-4,4-diphenylheptan-3-one (METHADONE®). Therapeutic agents also include, for example, agents that reduce the extracellular glutamate concentration such as, without limitation, soluble EAAT2 receptor or antibodies that specifically recognize and bind to glutamate (e.g., anti-glutamate Ab).

In certain instances, an effective amount of a compound that inhibits complement or the activation of complement can be administered to an individual. Compounds that inhibit complement are known in the art and include, without limitation, Compstatin, APT070(MICROCEPT), soluble complement receptor 1 (sCR1), anti-C5 antibody, eculizumab (SOLIRIS®), and substituted dihydrobenzofurans, spirobenzofuran-2(3H)- cycloalkanes, and their open chain intermediates (see, for example, U.S. Patent No. 5,506,247).

In some instances, effective amounts of one or more antagonists of glutamate receptors and one or more compounds that inhibit complement can be administered to an individual. One or more antagonists of glutamate receptors and one or more compounds that inhibit complement can be administered simultaneously, or the one or more antagonists of glutamate receptors and the one or more inhibitors of complement can be administered sequentially. In certain instances, an antagonist of glutamate receptors and a compound that inhibits complement can be administered alternatively to an individual.

Routes of administering compositions to an individual are well known in the art and include, for example, parenteral, e.g., intravenous, intradermal, subcutaneous, oral (e.g., ingestion or inhalation), transdermal (topical), transmucosal, and rectal administration. A composition for administering to an individual typically is formulated to be compatible with its intended route of administration.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Part A

Example 1

Cell Lines and Transgenic Constructs

Major binding sites of NMO-IgG (and affinity-purified AQP4-specific rabbit IgG) in sections of normal adult human and mouse CNS tissues are where AQP4 is expressed in highest density, namely in the dystroglycan complex of the highly polarized plasma membrane of astrocytic foot processes. The reason AQP4 is readily visualized at those sites immunohistochemically is because of its ultrastructural organization at those sites in tightly packed arrays. In preliminary Western blot studies (with protein overloaded conditions), it was observed that the rat oligodendroglial-astrocytic progenitor cell line (CG4), when differentiated in vitro to astrocytic phenotype (stellate and expressing prominent cytoplasmic GFAP intermediate filaments), express minimal AQP4 immunoreactivity, and that two independent human astrocytoma cell lines (HTB-14 and CRL-17; obtained from ATCC) did not express detectable AQP4 by immunofluorescence or Western blot. Therefore, as the initial system to investigate in vitro the immunobiological consequences of IgG interacting with extracellular epitopes of AQP4, transfected human embryonic kidney cell line (HEK293) over-expressing full-length human AQP4 protein (fused at its N-terminus with green fluorescent protein [GFP]) was used. The parental HEK293 cell line does not express AQP4 constitutively, but it does express dystroglycan complex partner proteins of AQP4, which assure stable AQP4 insertion in the plasma membrane. Furthermore, the proximity of adjacent AQP4 homotetramers in the transfected cell's membrane mimics the close packing of epitopes in the highly polarized astrocytic foot process.

Example 2

Antibodies and Sera

Fluorochrome-conjugated goat IgGs were purchased from Molecular Probes (Alex-Fluor 546; human, mouse or rabbit IgG-specific, and Oregon Green; mouse IgG-specific) or Invitrogen (Cy5; rabbit IgG-specific). Conjugated monoclonal mouse IgGs (FITC; specific for human IgG subclasses, or Cy3; specific for glial fibrillary acidic protein and sodium channel) were obtained from Sigma, and unconjugated were obtained from BD Biosciences (Caspr1 and early endosome antigen-1 [EEA1]) and Dako, Denmark (human CD138). Goat IgGs monospecific for human IgG (TRITC-conjugated) or human IgM (FITC-conjugated) were from Southern Biotechnology. Rabbit IgG specific for AQP4 residues 249-323 was obtained from Sigma. Rabbit IgG specific for human C9neo was a gift from Dr. Paul Morgan (Cardiff, UK). Deidentified patients' sera were obtained from the Neuroimmunology Laboratory, Department of Laboratory Medicine and Pathology, Mayo Clinic Rochester, Minn.

Example 3

Immunostaining

All final preparations of live cells and sections of mouse tissue and autopsied human lymph node and brain tissues were mounted in PROLONG® Gold DAPI antifade medium (Molecular Probes). Fluorescent images were captured from a Zeiss LSM510 confocal microscope. Immunoperoxidase-stained sections were counterstained with hematoxylin and photographed from an Olympus DP-BSW microscope and DP70 digital camera system.

Live cells were exposed sequentially to 20% human serum or rabbit anti-AQP4 IgG diluted 1:1000, secondary antibody (1:500) and chilled 95% ethanol/5% acetic acid (15 minutes). Cells fixed in 10% formalin were permeabilized, blocked, and incubated in primary and secondary antibody probes. Tissues dissected from perfused mice were post-fixed overnight in 4% paraformaldehyde, held 24 hours in 30% sucrose, frozen in OCT medium, sectioned (8 μm) and air-dried, incubated sequentially in 10% normal goat serum containing 0.1% Triton X-100 (30 minutes), primary antibody (18 hours) and secondary antibody (1 hour; room temperature). Autopsied human lymph node and brain tissues, fixed in 10% formalin and embedded in paraffin, were deparaffinized, sectioned (5 μm), washed in bi-distilled water and steam-heated. Sections were incubated with 10% normal goat serum (1 hour) and then overnight at 4° C. with primary antibody (anti-CD138 at 1:50; anti-IgG at 1:750; anti-IgM at 1:200).

Example 4

Antigen Modulation Assay

Complement was inactivated in the serum of patients and control subjects by incubating the serum for 30 minutes at 56° C. Time-lapse photomicrographs of living cells were captured at 15 minute intervals for 24 hours. Media containing human serum were replaced at 16 hours with fresh media, with or without cycloheximide (0.25 μg/mL). Test sera were added to the culture media for either 16 hours at 37° C. or 1 hour at 4° C. Cells were washed, exposed 30 minutes to Alexa-Fluor 546-labeled anti-human IgG (1:500), washed again, fixed in chilled 95% ethanol/5% acetic acid, rinsed in PBS, and stained with Hoescht (1 μg/mL).

Example 5

Complement Activation Assays

GFP-AQP4-HEK 293 cells were incubated for 2 hours on ice with 20% heat-inactivated control or NMO patients' serum. Cells were washed with chilled DMEM media and exposed to 20% fresh (or heat-inactivated) normal human serum (as complement source) for 45 minutes at 37° C. After rinsing and fixing (10% formalin, 4 minutes), cells were incubated sequentially at room temperature in 0.1% 3-[(3-cholamidopropyl) dimethylammonio]-1-propanesulfonate (1 minute), 10% normal goat serum and rabbit anti-human C9neo antibody (30 minutes), washed and incubated in labelled anti-rabbit IgG. To evaluate complement's effects on membrane integrity, test pools of human serum were added to the cells at 4° C. (for 1 hour). After subsequent incubation for 90 minutes at 37° C. (95% air/5% $CO_2$) in fresh or heat-inactivated Low-Tox-H rabbit complement (Cedarlane Lab; 20% final concentration), the monolayer was examined and photographed by transmitted bright field imaging. To quantitate complement-mediated membranolytic activity by flow cytometric analysis after sequential exposure to serum (30 minutes at room temperature) and complement (37° C. for 30 minutes), the cells were lifted with trypsin, washed and suspended in chilled buffer (10 mM Hepes/NaOH pH 7.4; 140 mM NaCl; 2.5 mM $CaCl_2$) containing 0.5 μg propidium iodide (BD Biosciences) and held in the dark for 15 minutes before analysis. Fold increase in membrane permeability was determined by comparing the percentage of propidium iodide permeable GFP-positive cells to propidium iodide-permeable GFP-negative cells. In the absence of antigen-specific activation of complement, the fold increase in membrane permeability was less than 1.25 (125%).

Example 6

IgG Depletion and Purification

IgG was depleted from serum pools using protein G-agarose beads (2 hours at 4° C.). IgG-depleted serum was used at a concentration of 20% in the complement assay. IgG eluted from washed protein G beads in 0.1 M acetic acid was neutralized, dialyzed against PBS and concentrated using Centricon YM-3 filter devices (Millipore). IgG concentrations were determined by rate nephelometry.

Example 7

Time-Lapse Photomicrographs

GFP-AQP4-HEK293 cells were seeded onto optical quality glass bottom plates (MatTek) and exposed to 20% control or NMO patients' serum. Time-lapse photomicrographs of the living cells were captured at 15 minute intervals for 6 hours using a Zeiss LSM510 microscope stage held at 37° C. in 95% air/5% $CO_2$. Z-series imaging was performed for each time point.

Example 8

NMO-IgG Initiates Endolysosomal Degradation of AQP4

A prerequisite for IgG to affect organ-specific pathogenicity is its capacity to bind to specific epitopes accessible on the surface of living target cells. When transfected target cells expressing surface AQP4 were exposed to a pool of NMO patients' sera (at 4° C. to restrict membrane fluidity), IgG bound to the plasma membrane in a linear pattern that co-localized with GFP-AQP4. Serum IgG from control patients did not bind detectably to the cell surface and a control rabbit IgG specific for AQP4 cytoplasmic epitopes did not bind unless the plasma membrane was permeabilized. NMO patients' serum IgG did not bind to vector-transfected control HEK-293 cells. Thus, NMO patients' IgG binds specifically to the extracellular domain of AQP4.

To evaluate the influence of this IgG on plasma membrane AQP4, the distribution of GFP-AQP4 was recorded after exposure to patients' serum at 37° C. Control human serum had no effect on GFP-AQP4, but NMO patients' sera containing AQP4-specific-IgG resulted in rapid disappearance of GFP-AQP4 from the plasma membrane. The phenomenon's temperature dependence is consistent with modulation of surface antigens through intermolecular cross-linking by bivalent IgG. Serial confocal images of living cells held at 37° C. for 16 hours in serum lacking AQP4-IgG were indistinguishable from images of untreated cells with respect to GFP-AQP4 fluorescence intensity and localization. Cells exposed to NMO patients' serum underwent a striking redistribution within 5 minutes. The homotetrameric structure of AQP4, with multiple repeated epitopes in the extracellular domain, and the proximity of individual AQP4 homotetramers provide an optimal target for rapid surface clearance from the plasma membrane by antigen-specific IgG. Plasma membrane fading was accompanied by green fluorescent vesicle accumulation in sub-plasmalemmal cytoplasm. After 20 minutes, GFP-AQP4 aggregated in ring-like structures. At 5 hours, when plasma membrane fluorescence was no longer detectable, these had coalesced into large cytoplasmic aggregates. Removal of the patients' serum at 16 hours resulted in rapid reappearance of GFP-AQP4 in sub-plasmalemmal vesicles, presumably en route from the endoplasmic reticulum. By 4 hours, GFP-AQP4 was visible in the plasma membrane and, by 12 hours, it had attained normal surface density. When cycloheximide was added at the time of withdrawing patients' serum, no GFP-AQP4 was seen on the plasma membrane during 12 hours of observation. This implies that the "reversal" of the autoantibody's effect was dependent on new protein synthesis.

The fate of GFP-AQP4 cleared from the plasma membrane after exposure to NMO patients' serum was followed by probing with an antibody specific for an early endosome antigen. In the absence of serum, early endosomal vesicles did not colocalize with GFP-AQP4. However, after 30 minutes exposure to NMO patients' serum, early endosomal vesicles acquired green fluorescence. Early endosomal vesicles did not acquire green fluorescence when cells were exposed for 2 hours to control sera. These results indicate that endocytosis initiated by the cross-linking of AQP4 by IgG binding at the cell surface targets AQP4 to the endolysosomal pathway for degradation.

Example 9

NMO-IgG Initiates Complement Activation

Activation of the classical complement cascade is another potentially pathogenic outcome of autoantibody binding to AQP4. This mechanism would increase the permeability of microvascular endothelium, promote inflammatory cell infiltration, and possibly inflict focal damage to astrocytic endfeet in central nervous system regions enriched in AQP4. Surface membranes of transfected cells were evaluated by indirect immunofluorescence for deposition of the "C9neo" epitope created by the polymerizaton of multiple perforin-like C9 molecules in assembling the terminal membrane attack complex of complement. In the presence of NMO patients' sera and active human complement, C9neo was clearly visualized in the plasma membrane of HEK-293 cells expressing AQP4, but was not visualized in the absence of disease-specific serum, in the presence of inactive human complement, or in control cells transfected with GFP-vector. These data indicate that NMO patients' sera contain an AQP4-specific antibody capable of activating the complement cascade. Reagents specific for human IgG subclasses revealed that AQP4-specific serum IgG was, in all NMO-IgG positive patients tested, exclusively IgG1, which is a major complement-activating IgG subclass in humans.

Preliminary experiments indicated that membrane lysis conditions had to be rigorously controlled to evaluate functional evidence for antigen-specific complement activation by NMO-IgG on membranes of living cells expressing AQP4 in high density. The GFP-AQP4 transfected target cell line was a mixed population of GFP-positive (AQP4+) and GFP-negative (AQP4−) cells. In the presence of control human serum, phase microscopy revealed healthy AQP4+ and AQP4− cells in an adherent monolayer. When the target cells were pre-exposed to disease-specific patients' serum (on ice for 2 hours) before adding complement for 90 minutes at 37° C. (conditions used for the C9neo visualization), all green cells disintegrated rapidly. Therefore, a standardized commercial preparation of rabbit complement, in limited concentration, was used. The cells were pre-exposed to patient or control serum at 4° C. for 1 hour before adding fresh or heat-inactivated complement. In the presence of NMO patients' serum, adherent cells that visibly expressed GFP were selectively lost. Provided that complement was active and present more than 30 minutes, most AQP4+ cells were rounded and floating. Control human serum did not visibly affect either adherent population regardless of complement activity. Thus, the cytolytic activity of NMO patients' serum depended on both complement activity and AQP4 expression in target cells.

Figure 1:
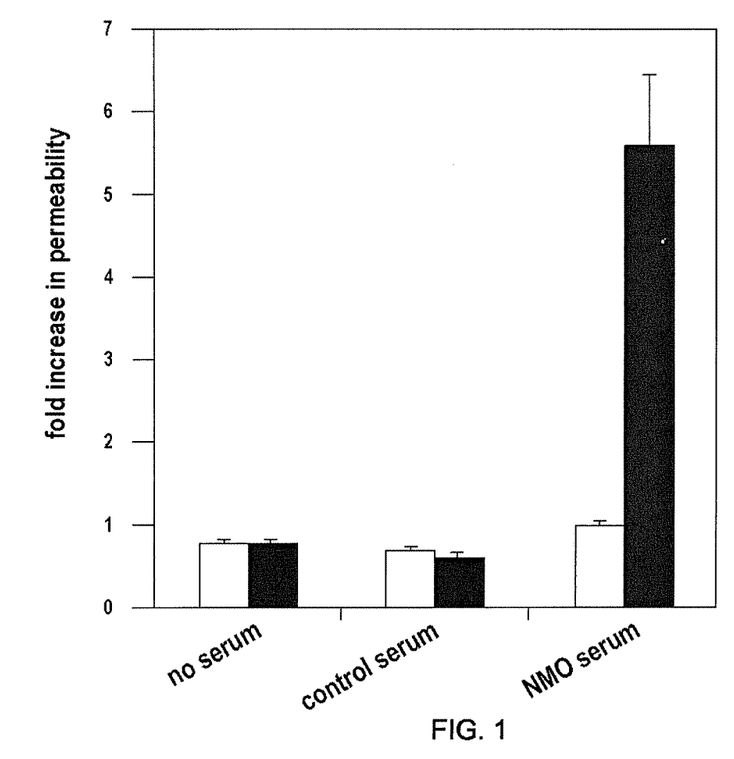
FIG. 1 is a graph showing the quantitation of membrane cytotoxicity induced by NMO serum and active complement (30 minutes at 37° C.). Results were the average of seven independent experiments each using an individual serum pool from 10-15 different NMO patients or from approximately 350 control patients with miscellaneous disorders.

Quantitation of target cell membrane lesioning by complement using flow cytometric analysis (indicated by permeability to the red dye, propidium iodide) necessitated further attenuation of complement activation. Therefore, cells were pre-exposed to patients' (or control serum) at room temperature for 30 minutes (rather than 1 hour at 4° C.) to allow some reduction of AQP4 antigen density by antigenic modulation before adding the complement. Cells were then incubated with complement at 37° C. for only 30 minutes before harvesting for analysis of green and red fluorescence intensities. Exposure to active or inactive complement had no effect on either AQP4+ or AQP4− cells in the presence of control patients' serum (FIG. 1). NMO patients' serum had no effect on membrane integrity when complement was inactivated regardless of whether or not AQP4 was expressed in the target cells. However, with active complement, there was an average 5.6 fold (560%) increase in the membrane permeability of AQP4+ cells compared with AQP4− cells (FIG. 1). Thus, the cytotoxicity of NMO patients' serum depended on surface expression of AQP4 and the availability of active complement.

Example 10

AQP4-Specific Autoantibodies are not IgM Class

Vasculocentric deposits of IgG, IgM and complement are a hallmark of histopathological lesions found in central nervous system tissue of NMO patients. Because pentameric IgM has five Fc effector domains, it activates the complement cascade more efficiently than IgG, which has only a single Fc domain. Therefore, sera and cerebrospinal fluid of NMO patients were analyzed for AQP4-specific IgM. By indirect immunofluorescence evaluation on sections of AQP4-rich mouse tissues, none of 31 individual NMO patients' sera nor 28 NMO patients' cerebrospinal fluid specimens had detectable AQP4-specific IgM. The flow cytometry assay was used to test for functional evidence of a complement-activating AQP4-specific IgM in serum from patients who were either positive or negative for AQP4 antibody of IgG class in the course of clinical immunofluorescence evaluation. Only the AQP4 IgG-positive sera (pools 1-4) were cytotoxic for AQP4+ cells. This cytotoxic activity was lost when IgG was depleted. Recovery of AQP4-specific complement activation restored by IgG from the original positive serum pools was proportional to the % total recovery of IgG from the Protein G-agarose beads.

To determine, immunohistochemically, the frequency of IgG and IgM production in inflammatory central nervous system lesions of NMO patients, accumulations of differentiated plasma cells were investigated using fluorochrome conjugated anti-human IgG and IgM class-specific reagents at limiting dilutions to avoid interference from background extracellular IgG and IgM. The medullary lesion of the illustrated patient contains abundant CD138-positive plasma cells and is in a region normally rich in AQP4. Plasma cells in the medullary lesion stained brightly for cytoplasmic IgG, but cytoplasmic IgM was not detected in any plasma cell. The immunoglobulin class specificity of the detection antibody reagents was confirmed on control sections of human lymph node tissue. Clusters of plasma cells exhibited bright cytoplasmic IgG and scattered plasma cells exhibited bright cytoplasmic IgM; very few cells were dual-labeled. In summary, these data suggest that the IgM deposited with IgG and complement products in AQP4-rich regions of NMO patients' central nervous system tissues is not AQP4-specific.

Example 11

AQP4-Enriched Astrocytic Processes Surround Nodes of Ranvier in Spinal Cord And Optic Nerve Involvement of myelin in the pathology of NMO remains to be explained in the context of AQP4. Freeze-fracture studies in the early 1970s defined "assemblies of particles" as an ultrastructural characteristic of astrocytic endfeet surrounding axons at nodes of Ranvier. These assemblies correspond to recently identified orthogonal arrays formed by AQP4 homotetramers in transfected cells. The proximity of AQP4-specific immunoreactivity in astrocytic membranes to nodes of Ranvier was analyzed by examining sections of mouse spinal cord and optic nerve tissues by confocal fluorescence microscopy. Immune rabbit IgG (affinity purified on AQP4 peptide) was used rather than NMO patient's serum because the latter is a complex mixture of multiple autoantibodies, and is not amenable to affinity purification because it binds only to native AQP4 and not to denatured membrane-extracted AQP4 or synthetic AQP4 polypeptides. AQP4 was localized with respect to nodal regions by simultaneously immunostaining sodium channels, which are densely concentrated in the nodal axonal membrane (or Caspr1, an abundant paranodal protein), and glial fibrillary acidic protein (GFAP), the cytoplasmic intermediate filament of astrocytic processes. In both spinal cord and optic nerve, AQP4 immunoreactivity was intense near astrocytic elements and encircled periodic axonal segments expressing sodium channel immunoreactivity. The concentric paranodal AQP4 immunoreactivity was brighter than the background mesh pattern of astrocytic AQP4 characteristic of central nervous system white matter and was devoid of GFAP, which astrocytic foot processes lack. The extracellular space surrounding astrocytic processes is enlarged in the region of the axon segment bearing sodium channels. The juxtaposition of intense AQP4 and Caspr1 immunoreactivities is consistent with extension of the astrocytic foot process beyond the node of Ranvier into the paranode.

Part B

Example 1

Cell Lines and Transgenic Constructs

Primary astrocytes isolated from cerebral cortices of P1-3 rats, and the rat brain-derived 0-2A progenitor cell line, CG-4, were grown as previously described (Louis et al., 1992, J. Neurosci. Res., 31:193-204; Garlin et al., 1995, J. Neurochem., 64:2572-80). The GFP-AQP4 construct and stably transfected human embryonic kidney cell lines (HEK-293) were described previously (Lennon et al., 2005, J. Exp. Med., 202:473-7; Hinson et al., 2007, Neurology, 69:2221-31). AQP5 was amplified from a human salivary gland cDNA library, inserted into pEGFP-N1 vector (Clontech) and transfected (Fugene 6) HEK-293 cells with the parent vector or vector containing AQP5 transgenes. Stable clones were maintained in DMEM supplemented with 10% bovine calf serum and antibiotics.

Example 2

Antibodies and Human Sera

Fluorochrome-conjugated goat IgGs were purchased from Molecular Probes (Alex-Fluor 546; human, mouse or rabbit IgG-specific, and Oregon Green; mouse IgG-specific) or Invitrogen (Cy5; rabbit IgG-specific), and goat IgGs monospecific for human IgG (TRITC-conjugated) or human IgM (FITC-conjugated) from Southern Biotechnology. Rabbit IgG specific for: AQP4 (residues 249-323) was purchased from Sigma, and rabbit IgG specific for EAAT1 and EAAT2 was purchased from Santa Cruz Biotechnologies (for Western blotting and immunoprecipitation) or AbCam (for immunofluorescence). Mouse monoclonal IgGs were purchased from AbCam (anti-EEA1), Sigma (anti-GFAP conjugated to Cy3), Transduction Labs (anti-EAAT2) and Santa Cruz Biotechnologies (anti-GFP). De-identified sera from NMO and control patients were obtained, with Mayo Clinic IRB approval, from the Neuroimmunology Laboratory, Department of Laboratory Medicine and Pathology, Mayo Clinic Rochester, Minn.

Example 3

Immunostaining

Cell lines grown on glass coverslips were rinsed in PBS and fixed in 4% PFA for 20minutes at room temperature. After holding 30 minutes in 9% normal goat serum/0.1% triton X-100, the cells were held at 4° C. overnight in defined antibodies diluted in 10% normal goat serum, then washed in PBS, and held 60 minutes at room temperature in appropriate secondary antibody diluted in 10% normal goat serum. After washing in PBS and mounting on a slide with PROLONG® Gold DAPI antifade medium (Molecular Probes), fluorochrome-labeled cells were imaged using a Zeiss LSM510 confocal microscope.

Sections of archival CNS tissues derived from control and NMO patients (5 µm, formalin-fixed and paraffin-embedded) were stained with haematoxylin and eosin (HE), Luxolfast blue-periodic acid-Schiff (LFB/PAS) or Bielschowsky silver impregnation. Avidin-biotin-based immunohistochemistry was performed without modification by incubating tissue sections 1 hour with 10% normal goat serum, then holding overnight at 4° C. with and without primary antibodies.

Example 4

Antigen Modulation Assay

Cells were dispensed onto glass coverslips coated with laminin (CG-4) or poly-L-lysine (HEK-293 and primary rat astrocytes; Biocoat, BD Biosciences). After at least 48 hours, control or NMO serum was added to 20% final concentration (with complement inactivated by holding 30 minutes at 56° C.) and the cells were then processed for immunofluorescence analysis.

Example 5

Complement Membrane Lesioning

Growth medium of confluent primary astrocytes growing in 6-well plates was replaced with fresh medium containing 20% NMO or control sera. After 15 minutes at room temperature, fresh or heat-inactivated complement (Low-Tox-H rabbit complement; Cedarlane Labs; final concentration 20%) was added and held for 40 minutes at 37° C., then processed for flow cytometric analysis.

Example 6

Glutamate Uptake Assay

Na+-dependent radiolabeled glutamate uptake was measured using primary astrocytes grown to confluence in 24-well dishes (Lin et al., 2001, Nature, 410:84-8). After rinsing with 50 mM Tris-HCl and 320 mM sucrose, pH 7.4, control wells were incubated for 15 minutes with 10 mM unlabeled L-glutamate, then L-[3H]glutamate (0.1 µCi, GE Healthcare, specific activity=55.0 µCi/nmol) was added in 25 mM NaHCO$_3$, 5 mM KCl, 1 mM KH$_2$PO$_4$, 1 mM MgSO$_4$, 2 mM CaCl$_2$ and 555 mM D-glucose, pH 7.4, with or without Na+(Kreb's buffer containing 120 mM NaCl, or 120 mM choline chloride, in 25 mM Tris, 5 mM KCl, 1 mM KH$_2$PO$_4$, 1 mM MgSO$_4$, 2 mM CaCl$_2$ and 555 mM D-glucose, pH 7.4). Both buffers contained 40 µM unlabeled glutamate. After 5 mins at 37° C., the cells were transferred to 4° C., washed extensively with PBS, lysed in 0.1 M NaOH and uptake of radiolabeled glutamate was measured using a Beckman LS 6000SC scintillation counter. For all experimental conditions, quadruplicate assays were performed and glutamate uptake was calculated as counts/min/well, with and without Na+.

To assay glutamate uptake in GFP vector and GFP-AQP4 stable HEK-293 cells, an alternative HEK-293-optimized protocol was used (Jensen et al., 2004, Biochem. Pharmacol., 67:2155-27). EAAT2-specific transport was defined as the difference in glutamate uptake between GFP vector cells and GFP-AQP4 transfected cells.

Example 7

Isolation of RNA and RT-PCR analysis

Total RNA was isolated from trizol-lysed cells, and double stranded cDNA were generated using Superscript III First Strand Synthesis kit with random hexamer primers (according to Invitrogen protocols). To avoid amplifying contaminating genomic DNA, primer pairs were used that anneal in adjacent exons: AQP4 (F5'-TGC ACC AGG AAG ATC AGC ATC G-3' (SEQ ID NO:1) and R5'-CAG GTC ATC CGT CTC TAC CTG-3' (SEQ ID NO:2)) and EAAT2 (F5'-GGT GGA AGT GCG AAT GCA CGA CAG TCA TC-3' (SEQ ID NO:3) and R5'-CCT CGT CTG GCG GTG GTG CAA CCA GGA C-3' (SEQ ID NO:4)). Beta-actin was amplified as a control.

Example 8

Immunoprecipitation and Western Blot

Protocols were as previously described (Lennon et al., 2005, J. Exp. Med., 202:473-477). Commercial antibodies (AQP4, EAAT1, EAAT2 or GFP, 2 µg/mL), or human sera (a high titer pool of NMO patient or control patient sera, 30 µL/mL) were used as probes. Immune complexes released from protein G-agarose were resolved by electrophoresis (4 15% gradient polyacrylamide, room temperature). Trans-blotted, blocked proteins were exposed for 1 hour to IgG specific for: GFP (1:1,000), AQP4 (1:500), EAAT1 (1:200), actin (1:2000) or EAAT2 (1:200), then probed with horseradish peroxidase-conjugated goat anti-mouse IgG or goat anti-rabbit IgG, and detected bound IgG autoradiographically (SuperSignal West Pico Chemiluminescence, Pierce).

Example 9

Statistical Analysis

Significance was calculated using Student's t-test (2-tailed).

Example 10

NMO-IgG Binding to Primary Astrocytes Induces AQP4 Modulation and Complement Activation AQP4 distribution was monitored after applying NMO or control serum to cerebral astrocytes. Serum containing NMO-IgG, but not control serum, induced rapid down-regulation of surface AQP4. AQP4 coalesced in cytoplasmic vesicles, reminiscent of those observed in GFP-AQP4-transfected non-neural cells exposed to NMO-IgG.

Figure 2A:
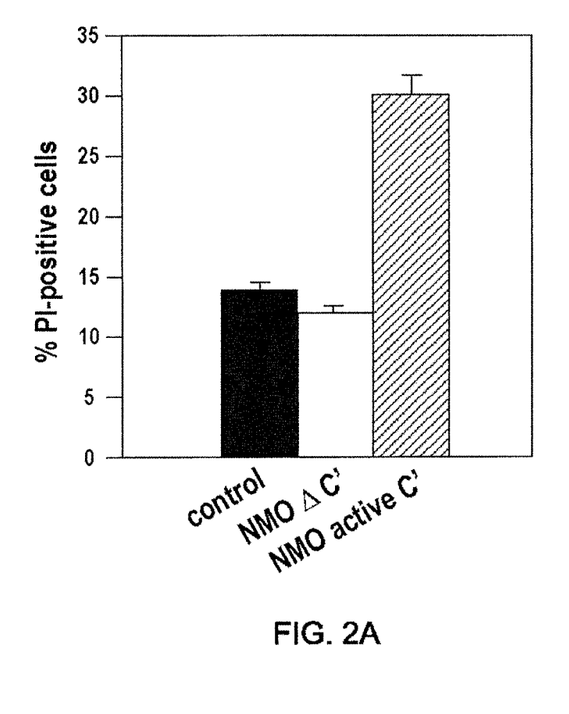

The complement-activating capacity of NMO-IgG binding to astrocytic AQP4, determined by including complement with NMO or control serum, was evaluated and the cells processed for flow cytometric analysis of propidium iodide influx. In the presence of NMO-IgG and active complement, plasma membrane permeability increased approximately 2 fold (p<0.007; FIG. 2A). With heat-inactivated complement, no discernible effect was observed with control serum or NMO serum (FIG. 2A). Activation of early complement components by IgG binding to the extracellular domain of AQP4 in astrocytes would increase CNS microvascular endothelial permeability and promote inflammatory cell infiltration. Assembly of the final membrane attack complex might focally damage endfeet, where AQP4 is expressed most highly. However, rich endowment of astrocytic membranes with complement regulatory proteins, as has been reported, may explain their relative resistance to AQP4-IgG-dependent lysis in this study, in comparison to AQP4-transfected HEK-293 cells.

Example 11

NMO-IgG Attenuates Na+-Dependent Glutamate Uptake in Astrocytes

Figure 2B:
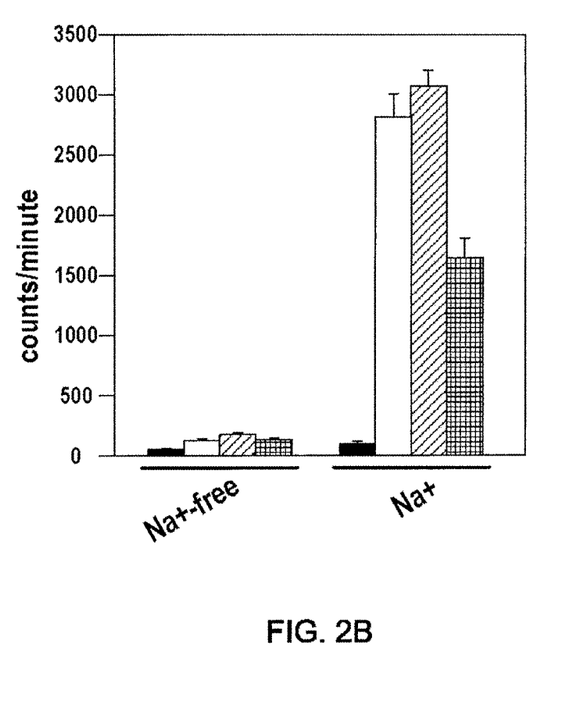

Na+-dependent glutamate transport in astrocytes exposed to NMO or control sera (FIG. 2B) was compared. Uptake of L-[$^3$H]glutamate was minimal (<200 counts/minute) in the absence of Na+ or when excess unlabeled glutamate was present. In the presence of Na+, L-[$^3$H]glutamate uptake was increased to approximately 3000 counts/minute in cells unexposed to serum or exposed to control patient serum (FIG. 2B). These results are consistent with the uptake of L-[$^3$H]glutamate being Na+-dependent and glutamate-specific. When serum containing NMO-IgG was added in these experimental conditions, L-[$^3$H]glutamate uptake was reduced by approximately 50% (p<0.0003; FIG. 2B).

Example 12

NMO-IgG Down-Regulates Both EAAT2 and AQP4 from the Surface of Differentiated Type-2 Astrocytic Cells Attenuation of astrocytic L-[$^3$H]glutamate uptake after exposure to NMO-IgG parallels loss of AQP4 protein. To investigate the possibility that EAAT2 protein may be lost secondary to loss of surface AQP4, EAAT2-specific IgG was used to follow the fate of EAAT2 after exposing astrocytes to NMO-IgG. Consistent with previous reports, it was confirmed that EAAT1 and EAAT2 glutamate transporter levels in primary rat astrocyte membranes are too low to detect by immunofluorescence staining. Therefore, EAAT2 expression was investigated in the bipotential glial cell line, CG-4, derived from O2-A progenitor cells in the developing rat CNS. In prescribed culture conditions (Louis et al., 1992, supra), CG-4 cells differentiate into type-2 astrocytes. In proliferation-promoting medium (containing bFGF and PDGF), the cells (CG4-PM) lack GFAP intermediate filaments. However, in medium with growth factors replaced by a high concentration of fetal bovine serum, type-2 astrocyte differentiation was evident in the cells (CG4-AM) by morphology and GFAP-immunoreactivity. In cells grown 7 days in astrocyte differentiation medium, plasma membrane expression of both AQP4 and EAAT2 was enhanced. However when NMO serum was added to CG4-AM cells at day 7, both AQP4 and EAAT2 were depleted from the plasma membrane. Addition of control sera in identical conditions did not discernibly affect expression of either AQP4 or EAAT2. Concomitant loss of both EAAT2 and AQP4 plausibly explains the reduced glutamate transport that was observed in cultured astrocytes exposed to NMO-IgG.

Example 13

EAAT2 Expression is Up-Regulated when AQP4 Protein Expression is Induced In Non-Neural Cells AQP4 and EAAT2 are both enriched in the astrocytic endfoot membrane. This finding that both AQP4 and EAAT2 are depleted from plasma membranes of cultured astrocytes exposed to NMO-IgG is consistent with the notion that EAAT2 expression depends on AQP4 expression. To further evaluate the relationship between AQP4 and glutamate transport, the HEK-293 non-neural cell line was studied, comparing EAAT2 expression in cells stably expressing GFP, GFP-AQP4, or a non-neural AQP, AQP5-GFP. EAAT 1 was readily detected in the plasma membranes of cell lines transfected with either GFP vector or GFP-AQP4. EAAT2 was not detected in GFP vector transfected cells, but EAAT2 was strikingly upregulated in the plasma membrane of cells transgenically expressing either AQP4 or AQP5.

To determine whether this observed increase in membrane EAAT2 and functional glutamate transport might reflect an increase in EAAT2 gene transcription or protein expression, EAAT2 transcripts were examined by RT-PCR. The three transfected HEK-293 lines expressed EAAT2 transcripts at similar levels. Western blot analyses supported the immunofluorescence observations that transgenic EAAT2 protein expression is upregulated when AQP4 or AQP5 is expressed in HEK-293 cells by comparison with cells transfected with vector alone. Expression of EAAT2 protein on the surface of cells expressing AQP might be increased through upregulated mRNA translation or, alternatively, through a post-translational modification increasing EAAT2 protein stability or trafficking to the plasma membrane. These complementary observations accord with reports that EAAT2 protein expression is restricted to astrocytes, despite ubiquitous expression of EAAT2 mRNA. It was concluded that restriction of EAAT2 expression to the plasma membrane of astrocytes is determined by dependence on astrocytic AQP expression.

Figure 3:
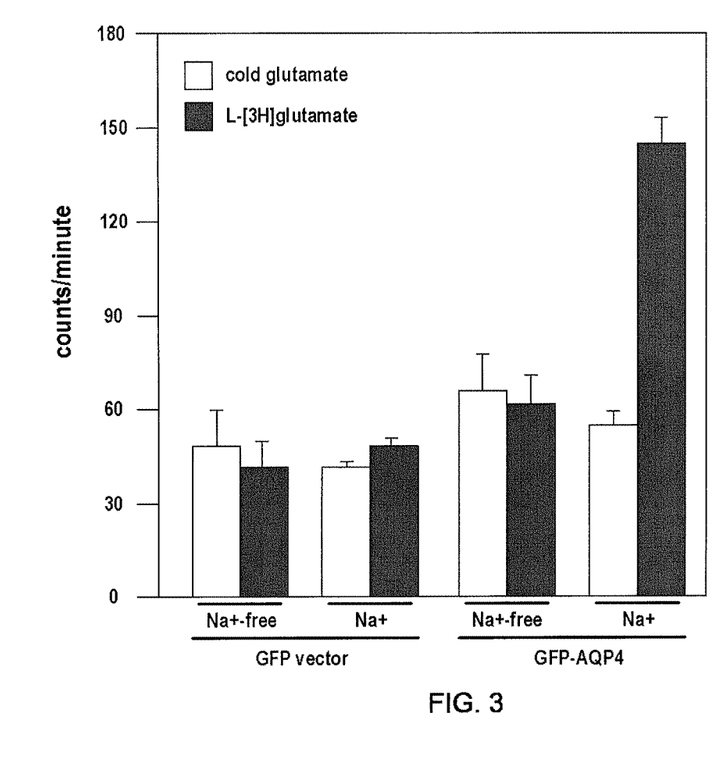
FIG. 3 demonstrates that expression of aquaporin proteins in HEK-293 cells induced EAAT2 protein expression. Glutamate transport: GFP-AQP4 cells took up approximately 3 fold more L-[$^3$H]glutamate than vector-transfected cells (note Na+-dependence). All experiments were performed a minimum of two times.

These results confirmed that upregulated EAAT2 protein in GFP-AQP4 transfected cells was functional by demonstrating that GFP-AQP4 cells imported 2-3 fold more glutamate via the Na+-dependent pathway relative to GFP vector cells (p<0.0002; FIG. 3). It is noteworthy that glutamate transport in Na+-containing buffer was unchanged in GFP vector cells compared to GFP-AQP4 (FIG. 3). It was anticipated that constitutively expressed EAAT1 in both cell lines would confer higher glutamate transport in GFP vector cells in Na+-containing buffer than in buffer lacking Na+. However, uptake of glutamate was unaffected in the presence of Na+, suggesting that EAAT1 expressed constitutively in these cells is not functional.

Example 14

Plasma Membrane Loss of EAAT2 Following Exposure to NMO Serum is EAAT2-Selective and is Dependent on the Presence of Both AQP4 Protein and NMO-IgG The data reported herein indicate that the concentration of AQP4 protein in the plasma membrane and Na+-dependent glutamate transport are both reduced by exposure of primary astrocytes to NMO-IgG. These observations in differentiated CG-4 type-2 astrocytes suggest that the effect on glutamate transport in primary astrocytes is due to plasma membrane loss of EAAT2. To further investigate the association between AQP4 and EAAT2, the effect of NMO and control sera on both EAAT1 and EAAT2 was evaluated. Control serum did not appreciably affect localization or expression of the EAAT2 transporter. However, serum containing NMO-IgG induced rapid surface down-regulation of both GFP-AQP4 and EAAT2. Higher magnification revealed apparent co-localization of EAAT2 and AQP4 in early endosomal vesicles, to which AQP4 translocation after exposure to NMO serum was previously demonstrated. The localization of AQP4 and the early endosome antigen-1 marker was evaluated after exposing the cells to NMO serum for 10 minutes. The white color that resulted when the images were merged suggested partial co-localization of AQP4 and EAAT2 in early endosomes. However, separate vesicles in close proximity or overlapping in the z axis would yield the same result.

The possibility that NMO serum might contain EAAT2-specific IgG in addition to AQP4 IgG was excluded by testing the effect of NMO serum on plasma membrane expression of EAAT2 in HEK-293 cells transfected with AQP5-GFP. Those cells express both EAAT1 and EAAT2, but are devoid of AQP4. Exposure to NMO-IgG did not affect the distribution of EAAT1 or EAAT2 in AQP5-GFP cells.

To investigate the specificity of EAAT2 down-regulation, the effect of NMO-IgG on the EAAT1 glutamate transporter, which is expressed constitutively in non-neural HEK-293 cells, was evaluated. NMO patient sera did not appreciably affect EAAT1 expression in these cells, in contrast to the loss of EAAT2 from the plasma membrane. These results imply a specific association between AQP4 and EAAT2 that does not exist for EAAT1. The rapid down-regulation of EAAT2 and AQP4 induced by NMO-IgG in GFP-AQP4-expressing cells and co-localization of both proteins in cytoplasmic endocytotic vesicles within 10 minutes is consistent with a direct effect of IgG on a surface macromolecular complex. The reduction in astrocytic glutamate transport accompanying AQP4 down-regulation after exposure to NMO-IgG further supports the idea that AQP4 and EAAT2 are associated functionally in the plasma membrane.

Example 15

AQP4 and EAAT2 Co-Immunoprecipitate

EAAT2 and EAAT1 are enriched in separate microdomains of the astrocytic plasma membrane; EAAT2 is enriched in regions that highly express AQP4. The data reported herein suggest that EAAT2 and AQP4 exist as a macromolecular complex. When exposed to NMO-IgG, both are translocated from the plasma membrane to an endolysosomal-targeted population of cytoplasmic vesicles. To evaluate potential physical interaction, GFP-AQP4 transfected cells was solubilized and the lysates were probed with EAAT2-IgG. Addition of protein G-agarose captured both EAAT2 and AQP4. Similar data was obtained using independent IgGs recognizing different EAAT2 epitopes. As a specificity control, results obtained using EAAT1-IgG as a probe for the cell lysates was compared. In contrast to EAAT2-IgG, EAAT1-IgG did not pull down AQP4. These results support the existence of AQP4 and EAAT2 as a macromolecular complex independent of EAAT1.

Example 16

Co-Localization of AQP4 and EAAT2 in CNS Tissue

The observations in primary astrocytes, type-2 differentiated CG-4 cells and transfected non-neural HEK-293 cells indicate that the interaction of NMO-IgG with AQP4 induces at least three possible outcomes, each potentially pathogenic: complement activation, down-regulation of AQP4, and coupled down-regulation of the EAAT2 glutamate transporter. The immunohistochemical analysis of nonpathologic human CNS tissue (both cortical and spinal cord) revealed that EAAT2, but not EAAT1, normally co-localizes with AQP4 in gray matter astrocytes and that EAAT2 is most enriched in spinal cord gray matter. These findings were reproducible.

Example 17

NMO Spinal Cord Lesions Lack Both AQP4 and EAAT2

Loss of AQP4 is a distinctive finding in both early and late lesions of NMO. NMO spinal cord tissue of normal appearance expresses normal levels of APQ4 and EAAT2 and lacks evidence of complement deposition. Lesioned NMO spinal cord gray matter contrasts to normal appearing gray matter by exhibiting markedly reduced EAAT2, in addition to AQP4 loss and deposition of complement activation products. Together, these findings are consistent with the absence of EAAT2 staining being a biological phenomenon within the NMO lesion. EAAT2 loss may partially account for the destructive involvement of spinal cord gray matter which is characteristic of NMO. Lesions in MS CNS tissues are typically not necrotic. The marked loss of EAAT2 described herein parallels loss of AQP4 in lesioned NMO spinal cord tissue and contrasts with the increases in EAAT2 and AQP4 reported in both active and chronic MS lesions. It was concluded that differences in regulation of glutamate homeostasis further distinguish NMO from classical MS.

Example 18

Concluding Remarks

The data presented herein from studies of living astrocytes, patient and control sera, normal human spinal cord tissue and spinal cord tissues from a patient with typical NMO, both non-lesioned and lesioned, provide the first evidence supporting a pathogenic role for NMO-IgG in disrupting glutamate transport. Because astrocytes are relatively tolerant to increased glutamate concentrations, disruption of glutamate homeostasis by NMO-IgG has particular excitotoxic potential for neurons and oligodendrocytes. A focal increase of extracellular glutamate levels secondary to NMO-IgG-induced down-regulation of AQP4 may suffice to injure or kill oligodendrocytes that express calcium-permeable glutamate receptors. Oligodendrocytes in the spinal cord and optic nerve, which are principal sites of demyelination in NMO, are particularly sensitive to changes in glutamate concentration. Modest elevation of extracellular glutamate concentration renders oligodendrocytes additionally susceptible to Ig-independent complement attack. The potential pathogenic sequelae demonstrated in this study for NMO-IgG binding to AQP4-rich membranes in primary astrocytes are both competing and cooperative. Depletion of AQP4 water channels in the plasma membrane would disrupt water homeostasis and promote edema. If complement were lacking, the consequences of impaired glutamate transport would be particularly deleterious for oligodendrocytes and neurons.

Outcomes of therapies directed at glutamate receptors have been unimpressive for neurodegenerative conditions where glutamate toxicity has been implicated in disease progression. However, demonstrating that the major astrocytic glutamate transporter, EAAT2, exists in a macromolecular complex with the AQP4 water channel and is down-regulated by AQP4-specific autoantibodies that are restricted to patients with the NMO-spectrum of CNS inflammatory autoimmune demyelinating disorders has unanticipated pathogenic implications for glutamate toxicity as a central mechanism in a spectrum of disorders which are commonly mistaken for MS. NMO is now recognized as a potentially reversible IgG-mediated attack on astrocytic water channels. The results that were obtained from studies of serum and spinal cord tissue of patients with NMO hold promise for novel therapeutic strategies for the management of NMO-spectrum disorders. For example, it might be feasible to ameliorate tissue damage in both grey and white matter if therapeutic upregulation of EAAT2 can be achieved in patients whose neurological dysfunction is attributable to AQP4 autoimmunity.

Example 19

Prognostic Utility of Functional Assays for NMO/AQP4-IgG

Preliminary data (Table 1) revealed a lack of correlation between serum levels of NMO-IgG (by immunofluorescence assay) and attack severity and between NMO-IgG immunofluorescence titers and complement activation quantified by flow cytometric analysis comparison with cells exposed to healthy control subjects' serum. In contrast, functional assays quantitating the outcome of NMO-IgG binding to cells expressing AQP4 have revealed significant correlation between the severity of an acute NMO attack and activation of complement. For the purposes of these studies, attacks were classified as "mild" when visual or limb impairment was minimal or when complete recovery occurred (Patients 1-6), and as "severe" when the attack resulted in residual blindness (from optic neuritis) or paralysis (from spinal cord inflammation) (Patients 7-12).

TABLE 1

| Individuals whose sera were tested | NMO Attack Severity | IF Titer | Complement-dependent lesioning of AQP4 + HEK293 cells (%) |
|---|---|---|---|
| Patients with acute attack | | | |
| 1 | mild | 1920 | 10 |
| 2 | mild | 240 | 15.9 |
| 3 | mild | 960 | 7.8 |
| 4 | mild | 960 | 19.1 |
| 5 | mild | 7680 | 12.3 |
| 6 | mild | 1920 | 19.2 |
| 7 | severe | 7680 | 59.8 |
| 8 | severe | 960 | 20.5 |
| 9 | severe | 1920 | 27.7 |
| 10 | severe | 3840 | 51.8 |
| 11 | severe | 15360 | 60.1 |
| 12 | severe | 7680 | 55.7 |
| Healthy Controls | | | |
| 1 | — | Negative | 7.5% |
| 2 | — | Negative | 8.2% |
| 3 | — | Negative | 9.1% |
| 4 | — | Negative | 8.0% |
| 5 | — | Negative | 11.6% |
| 6 | — | Negative | 7.7% |
| 7 | — | Negative | 7.6% |
| 8 | — | Negative | 9.9% |
| 9 | — | Negative | 7.6% |
| Multiple Sclerosis Controls | | | |
| MS 1 | — | Negative | 9.2% |
| MS 2 | — | Negative | 11.9% |
| MS 3 | — | Negative | 10.5% |
| MS 4 | — | Negative | 10.7% |
| MS 5 | — | Negative | 12.5% |
| MS 6 | — | Negative | 14.3% |
| MS 7 | — | Negative | 13.2% |
| MS 8 | — | Negative | 14.8% |
| MS 9 | — | Negative | 14.3% |

Measures of complement activation by NMO-IgG were significantly ($p<0.005$) associated with attack severity classification (mild or severe) but NMO-IgG titers were not ($p>0.05$). Quantitative functional effects of patient serum on AQP4-expressing cells can be assayed on cultured astrocytes, astrocytic cell lines or transfected non-neural cells. Correlation with clinical variables provides information pertinent to anticipated outcome of attack (e.g., relapse risk, attack severity (e.g., vision loss, paralysis), or extent of recovery).

Figure 4:
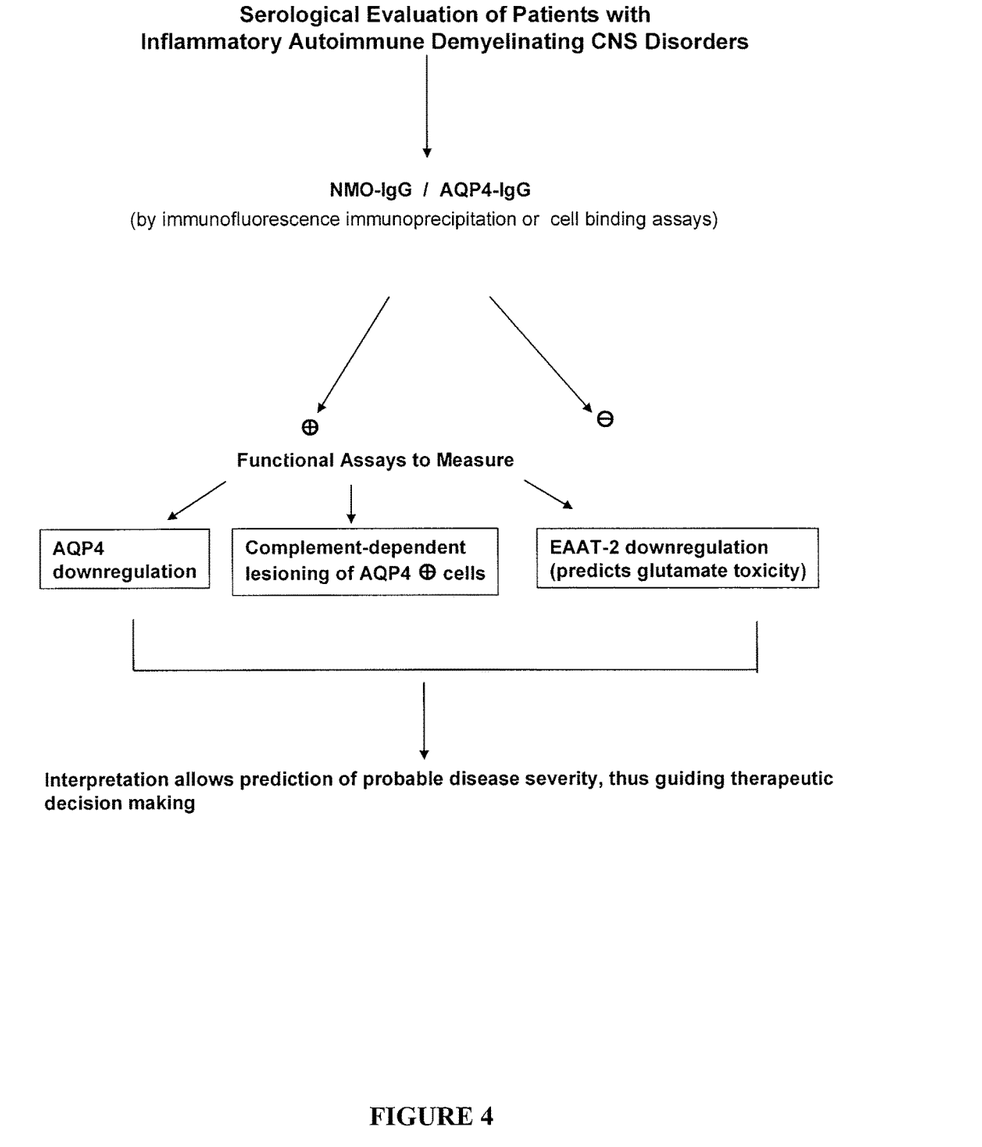
FIG. 4 shows a flow-chart showing pathways for serological evaluation of patients.

These data support an algorithmic approach for the serological evaluation of patients with inflammatory autoimmune demyelinating disorders of the central nervous system (FIG. 4). Seropositivity in initial immunochemical screening assays for NMO-IgG supports the diagnosis of an NMO spectrum disorder. Further testing of seropositive patients using functional assays (as demonstrated by the complement activation assay described above; and also by AQP4 and EAAT2 transporter modulating assays described herein) is anticipated to provide prognostic information guiding therapeutic decision making. It is also observed that AQP4-modulating assays are sufficiently sensitive to detect NMO-IgG in some clinically proven cases that are negative by immunochemical assays.

It is possible that diverse serological effects may occur in individual patients. For example, one patient's disease severity may correlate well with measures of AQP4 complement activation while another may correlate with measures of AQP4/EEAT2 downregulation. In future clinical practice, the choice of treatment for individual patients with NMO spectrum disorders may be determined by the individual's serological profile in functional assays of AQP4/NMO-IgG. For example, patients whose sera are highly complement activating may be ideal candidates for complement inhibitory therapies, or patients whose EAAT2 levels are significantly reduced may be ideal candidates for glutamate receptor antagonist therapies.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of treating an individual that has neuromyelitis optica (NMO), comprising:
   identifying an individual that is serologically positive for aquaporin-4 (AQP4)-IgG autoantibody; and
   administering eculizumab to the individual.

2. The method of claim 1, wherein eculizumab is administered intravenously.

3. A method of treating an individual that has NMO, comprising the steps of:
   identifying an individual that is serologically positive for aquaporin-4 (AQP4)-IgG autoantibody;
   determining the complement-activating capacity of AQP4-IgG autoantibody in a biological sample from the individual; and
   administering an effective amount of eculizumab to the individual.

4. The method of claim 3, wherein the eculizumab is administered intravenously.

5. A method for treating neuromyelitis optica (NMO), wherein said method comprises administering eculizumab to an individual identified as being serologically positive for an aquaporin-4 (AQP4)-IgG autoantibody.

6. The method of claim 5, wherein said eculizumab is administered intravenously to said individual.

* * * * *

UNITED STATES PATENT AND TRADEMARK OFFICE
CERTIFICATE OF CORRECTION

PATENT NO.      : 9,891,219 B2
APPLICATION NO. : 12/573942
DATED           : February 13, 2018
INVENTOR(S)     : Lennon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 457 days.

Signed and Sealed this
Twenty-fifth Day of September, 2018

Andrei Iancu
*Director of the United States Patent and Trademark Office*

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: Oligonucleotide

<400> SEQUENCE: 1
tgcaccagga agatcagcat cg                                       22

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide

<400> SEQUENCE: 2
caggtcatcc gtctctacct g                                        21

<210> SEQ ID NO 3
<211> LENGTH: 29
<212> TYPE: DNA
<213> ORGANISM: Artificial Sequence
<220> FEATURE:
<223> OTHER INFORMATION: Oligonucleotide

<400> SEQUENCE: 3
ggtggaagtg cgaatgcacg acagtcatc                                29

<210> SEQ ID NO 4
<211> LENGTH: 28
<212> TYPE: DNA
<213> ORGANISM: Artificial Sequence
<220> FEATURE:
<223> OTHER INFORMATION: Oligonucleotide

<400> SEQUENCE: 4
cctcgtctgg cggtggtgca accaggac                                 28